United States Patent [19]

Wang

[11] Patent Number: 5,458,575
[45] Date of Patent: Oct. 17, 1995

[54] PERFUSION CATHETER HAVING A CYLINDRICAL ARRAY OF BALLOONS

[75] Inventor: James C. Wang, Norton, Mass.

[73] Assignee: Boston Scientific Corp., Natick, Mass.

[21] Appl. No.: 224,910

[22] Filed: Apr. 8, 1994

Related U.S. Application Data

[63] Continuation-in-part of Ser. No. 17,763, Feb. 16, 1993, abandoned.

[51] Int. Cl.[6] ................................................. A61M 29/00
[52] U.S. Cl. ............................ 604/101; 604/96; 606/194
[58] Field of Search .......................... 604/96, 101, 102; 606/192, 194

[56] References Cited

U.S. PATENT DOCUMENTS

| | | | |
|---|---|---|---|
| 4,787,388 | 11/1988 | Hofmann | 606/194 |
| 4,878,495 | 11/1989 | Arayzel | 604/101 X |
| 4,983,165 | 1/1991 | Loiterman | 604/95 |
| 5,002,531 | 3/1991 | Bonzel | 604/96 |
| 5,102,416 | 4/1992 | Rock | 606/194 |
| 5,304,135 | 4/1994 | Shonk | 604/101 |
| 5,308,323 | 5/1994 | Sogawa et al. | 604/95 |
| 5,308,356 | 5/1994 | Blackshear, Jr. et al. | 606/194 |
| 5,330,528 | 7/1994 | Lazim | 623/1 |
| 5,342,301 | 8/1994 | Saab | 604/96 |

*Primary Examiner*—Corrine M. Maglione

[57] ABSTRACT

A perfusion catheter for insertion into a body conduit, especially an artery. The catheter comprises a shaft (5) having at least two lumens for delivery of fluid inflation medias and an array (1) formed of a plurality of radially disposed inflatable balloons (3) disposed in a cylindrical array around the shaft (5), each of the balloons (3) sharing a common wall (3a) with adjacent balloons (3). The balloons (3) are inflated by an array (1) of channels (11) and separated from each other by a web (19). There is at least one opening (17) between two adjacent channels (11) to allow the flow of fluids into the array (1). An internal chamber (31) is formed inside the array (1) by the movement of a wall (30) over the axis of the catheter whereby to enable a substantial increase of inflation forces against the body conduit in which the catheter is disposed.

11 Claims, 2 Drawing Sheets

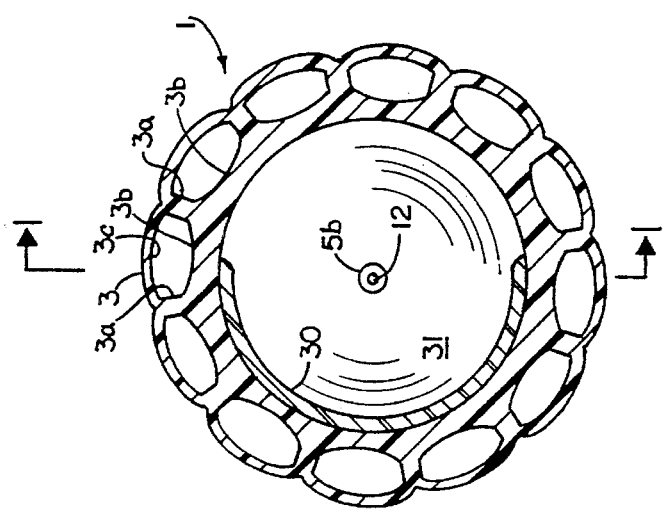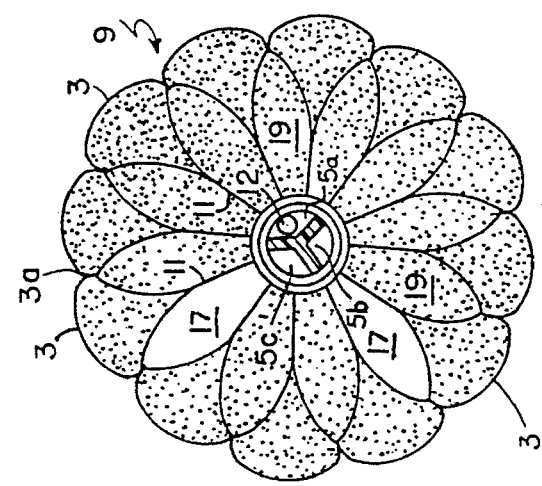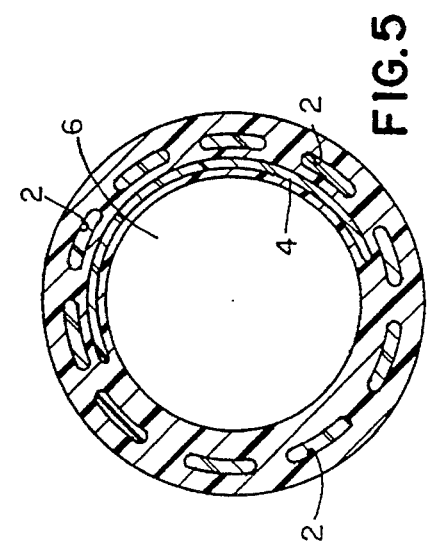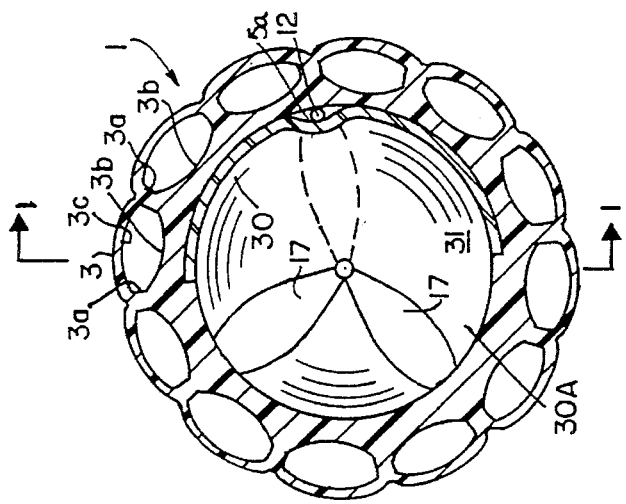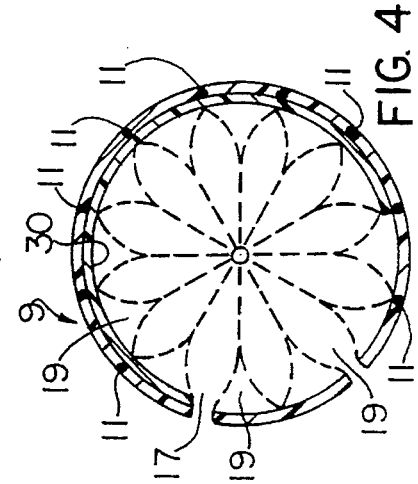

PERFUSION CATHETER HAVING A CYLINDRICAL ARRAY OF BALLOONS

RELATION TO OTHER APPLICATIONS

The present application is a continuation-in-part of my application, Ser. No. 08/017,763, filed Feb. 16, 1993 now abandoned.

BACKGROUND OF THE INVENTION

The present invention relates to catheters for placement in body conduits where there is a necessity to provide a continuous flow of body fluids past the catheter. The invention particularly relates to coronary dilation catheters for use in administering treatments to widen a constricted blood flow passage frequently caused by a stenosis in, for example, a heart valve or coronary artery.

A stenosis is a region of a blood vessel which has been narrowed to such a degree that blood flow is restricted. If the stenosis is severe, treatment is required to restore adequate blood flow and often such treatment requires surgery or angioplasty. Transluminal angioplasty is a procedure for treating a patient having a stenosis or constricted region in a coronary artery. Frequently the stenosis can be expanded so that the artery will permit an acceptable blood flow rate.

Coronary angioplasty includes the insertion of a balloon through a patient's artery to the arterial stenosis and injecting a suitable fluid into the balloon to inflate it and hence expand the stenosis radially outwardly and compress it against the artery wall. Angioplasty has become a successful alternative to coronary arterial bypass surgery. The stenosis is compressed radially outward against the arterial wall to increase the cross-sectional serves area of the artery so that the artery has an acceptable blood flow rate.

Ordinary balloon catheters have a balloon fastened around the exterior of a hollow catheter tube. A tubular shaft is fastened to the balloon and the balloon is in fluid flow relation with the interior of the shaft. The shaft provides a fluid supply for inflating the balloon.

Coronary dilation catheters previously used in coronary angioplasty have the disadvantage of completely occluding the flow of blood while the balloon is expanded in the artery. However complete occlusion of a coronary artery cannot be permitted for any significant time without incurring serious risk of damage to portions of the heart that must receive blood from the occluded artery. Thus the balloon is pressurized for only a short time before it is depressurized to permit resumption of blood flow through the region of the stenosis. The inflation durations currently used are limited and can range from 15 seconds to 3 minutes, depending on the patient being treated. The limited inflation time frequently is not sufficient to treat a stenosis and inflations must be repeated.

Further, even if the arterial lumen is successfully dilated the effect may be only temporary. Restenosis of the artery after treatment is not uncommon. The sustained inflation of the balloon catheter, rather than short multiple inflations, reduces the possibility of post treatment restenosis and other clinical abnormalities.

DESCRIPTION OF THE PRIOR ART

Catheters have been devised which allow blood to flow by them when they are inflated. Such catheters are called balloon perfusion catheters. Commonly such perfusion catheters have a perfusion shaft with a plurality of openings which permit blood flow through the artery during balloon inflation. The openings generally spirally circumscribe the perfusion shaft both proximally and distally of the balloon, each opening being radially offset from adjacent openings. The blood thus flows into the perfusion shaft to exit on the other side of the balloon. Such a catheter is described in the U.S. Pat. No. 5,087,247 to Horn et al. Another example of a perfusion catheter is disclosed in U.S. Pat. No. 4,581,017 to Sahota. The catheter described in Sahota involves the disposition of the several radially offset lobes which are individually inflatable by minor lumens that are disposed outside of the principle lumen. The blood passes by the lobes without entering a perfusion shaft. The pressure exerted against the stenosis is not uniformly distributed, however. Also the perfusion rate is somewhat limited especially when a long balloon is used. Generally, the tube through which the blood flows is small in size, 0.030 inches ID. It cannot be made larger since that would increase an already large profile (outer diameter) in the deflated balloon. When the defined profile of the deflated balloon is too large it cannot be used in tight lesions.

In my co-pending application mentioned above, I have found that the therein-described catheter can optimally be pressurized to only about 2 to 4 Atm. which may not always be sufficient for the dilation of some stenoses. In many angioplasty procedures it is desirable to use inflation pressures significantly higher then 4 Atm.

SUMMARY OF THE INVENTION

According to the present invention I have discovered that the inflatable perfusion catheter of my co-pending application utilizing a cylindrical array of radially disposed, individually inflatable balloons around a central opening can be inflated to considerably higher pressures to exert higher forces upon the body vessel being treated if the array has an internal, temporarily inflatable chamber disposed within it. As with the catheter of my co-pending application, when used to treat an arterial stenosis, the array of balloons can exert a substantially uniform radial pressure on the artery wall. With the catheter of the present invention, however, the inflation can be to substantially greater pressures in the order of 8 Atm which translates to significantly higher forces being exerted upon the stenosis. When the internal chamber is not inflated, the catheter allows the body fluids to flow through the central opening of the cylindrical array which enables the continuation of a high rate of body fluid flow. Force is continually exerted upon the stenosis even though it is relieved by periodic deflation of the internal chamber.

The high dilation pressure is a direct result of creating an internal inflation chamber within the cylindrical array of balloons. Inflation, in a preferred embodiment of the invention, is produced by forcing an inflation fluid between a movable wall and an interior wall of the array. By inflating the internal chamber and also pressurizing the balloons of the array, dilation under high pressure can be provided. The internal chamber can be periodically deflated (by evacuating the inflation fluids) to create a large conduit for body fluids to flow through. Since support for the outer walls of the balloon is provided by the inner walls of the array, the catheter can have a low external profile.

The internal chamber is preferably constructed by co-extruding the peripheral stripes necessary to form the cylindrical array of balloons as described in my co-pending application. A radially inwardly disposed secondary stripe is also co-extruded within the peripheral array. The secondary stripe is co-extruded in about 50% or more of the circumference of the extrusion. When the stripes are removed, they will leave cylindrically arranged balloon-forming ducts. A secondary duct is formed by the removal of the secondary stripe and is disposed radially inwardly from the balloon-forming ducts. Innermost of these ducts is a central opening through the body fluids can flow to provide the perfusion catheter. The wall of the secondary duct forms a flap that can shift across the central opening from adjacent one side of the inside of the balloon to the other side and back again. Movement is produced by evacuating the central opening which will cause the wall to shift from one side of the central opening to the other and form the internal chamber. The internal chamber is inside the array and can exert high forces upon the stenosis. When the internal chamber is deflated (by pressurizing the central opening) the wall will shift to its original position and allow the flow of body fluids. Additionally, the catheter of the present invention can have two sizes, one being achieved by inflating first the internal chamber and a larger one being achieved by inflating the array also.

In the manufacture of the catheter, a hollow tube of two or more dissimilar plastics material is co-extruded using conventional co-extrusion techniques. A discrete phase, that is the phase which serves as the precursor of the ducts (and which dictates their locations and shapes) is formed of high density polyethylene, Nylon, low density polyethylene or polyethylene copolymers. A continuous phase, that is the phase that will form the walls of the balloons with the discrete phase disposed therein, can be formed of Nylon, polyethylene terephthalate or high or low density polyethylene. High density polyethylene, low density polyethylene and polyethylene copolymers can be extruded within polyethylene terephthalate. Nylon can be co-extruded within the high or low density polyethylene. After the phases are co-extruded, the discrete phase is drawn from the continuous phase to leave the ducts inside the continuous phase.

Co-extrusion of two plastic materials is well known and conventional techniques are used for such processes. The essential criteria for matching of two plastics materials is that they not adhere to each other after extrusion and that the discrete phase can be withdrawn from the continuous phase and leave ducts therein. While co-extrusion is preferred to form the balloons, it is also possible to extrude tubes with the ducts already in them using known extrusion dies. Because the thickness of the precursors to the ducts are so narrow, normally between about 0.025 and 0.5 mm. within a tube having a wall thickness between about 0.07 and 1.0 mm. and outside diameter between about 0.25 and 5.0 mm., I have found that extrusion with preformed ducts is not always satisfactory and that co-extrusion is best.

The many other objects, features and advantages of the present invention will become apparent from the following description.

DESCRIPTION OF THE DRAWINGS

FIGS. 2A and 2B are a cross-sectional view of the perfusion catheter shown in FIG. 1 taken along the line 2—2. In FIG. 2A the internal chamber is not inflated while in FIG. 2B it is inflated.

FIG. 3 is an end view of the perfusion catheter showing the relative dispositions of the array of balloons, webs and channels in the proximal end of the catheter. The view is taken along the line 3—3 of FIG. 1.

FIG. 4 is a cross-sectional interior view of the array of balloons taken along the line 4—4 of FIG. 1.

FIG. 5 is a cross-sectional view of the extruded tubing prior to the removal of stripes that are co-extruded as the precursors of the openings within the tubing.

DESCRIPTION OF THE PREFERRED EMBODIMENTS

Figure 1:
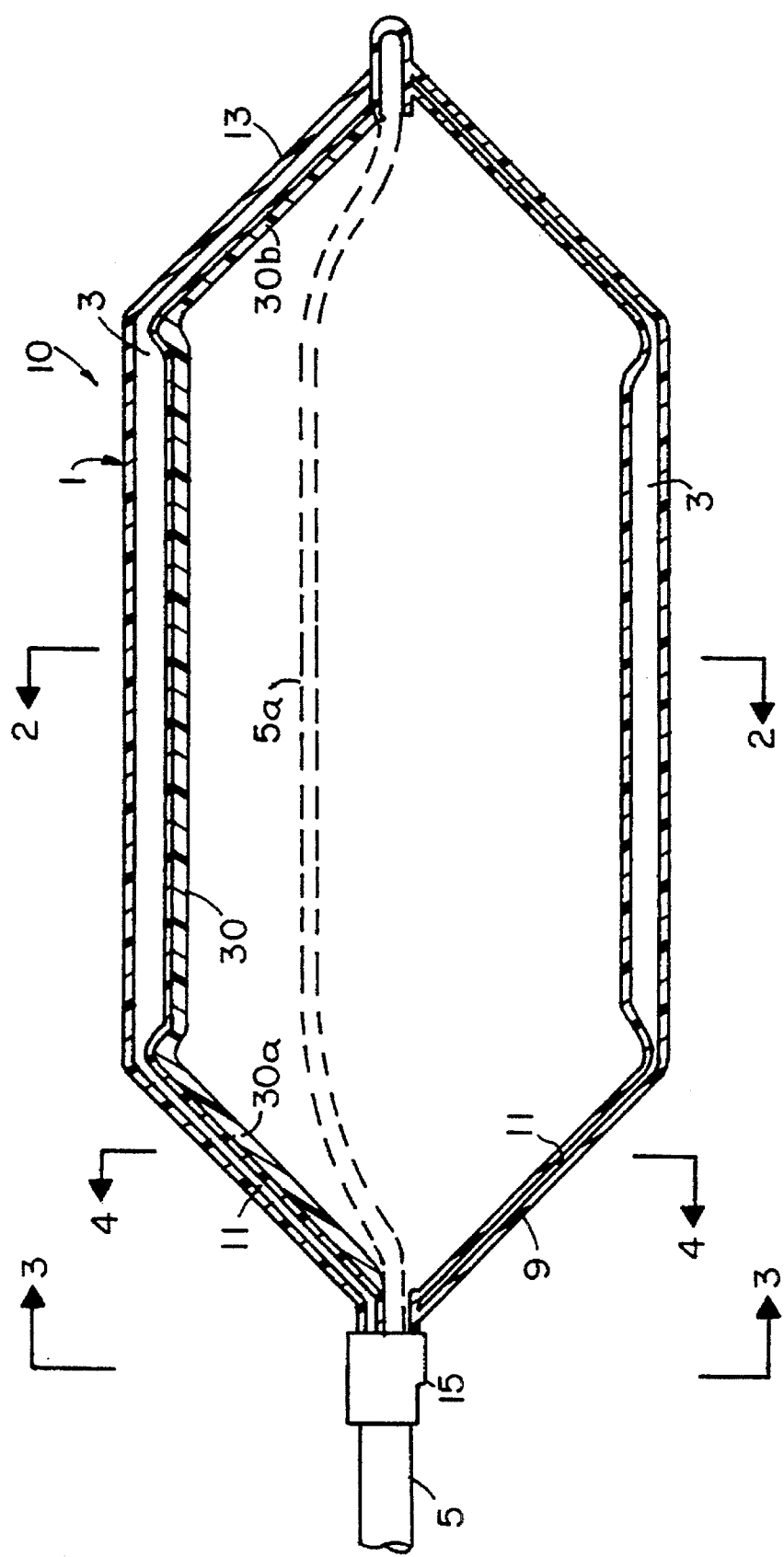
FIG. 1 is a cross-sectional view of a perfusion catheter in the inflated condition according to an embodiment of the present invention. The view is taken along the line 1—1 of FIG. 2.

Referring now to FIG. 1 the catheter 10 of the present invention includes an inflatable cylindrical array 1 of radially disposed balloons 3. Each of the balloons 3 in the array 1 are in fluid flow relation with one of the inflation lumens disposed in a shaft 5 as will be explained hereinafter. A hub 15 is disposed around the shaft 5 to secure the assembly. A proximal intermediate member 9 connects the hub 15 with the array of balloons 3. Channels 11 are formed in the proximal intermediate member 9 to provide fluid passageways between an inflation lumen within the shaft 5 and the interiors of the balloons 3. The inflation lumen may be one of several lumens in the shaft 5 as will be explained hereinafter.

The balloons 3 are also connected to a distal intermediate member 13. In the herein depicted embodiment a portion 5a of the shaft 5 is disposed centrally within the array 1 to provide support for the array 1 by means of the distal intermediate member 13 and also to house a guide wire 12. The wall 30 is disposed inside of the array 1 and is movable from one side of the interior of the array 1 to the other to form the internal chamber 31 which pressurizes the inside of the array 1 and expands it further to exert greater force against a stenosis. As the wall 30 moves to form an internal chamber 31, it carries with it sections which are integral with the distal and proximal intermediate sections of the catheter. While shaft 5a is shown as moving from adjacent the inner wall 3b to the middle of the internal chamber 31, in some embodiments, not shown, the shaft 5 can be terminated at the hub 15 and the array 1 and the distal intermediate member 13 can be self supporting.

Inflation of the balloons 3 causes the array 1 to expand from a folded arrangement around the shaft 5 to a cylindrical array that is spaced from the shaft 5 and provides an interior passageway for perfusion of fluids in the body conduit where the catheter is disposed. The expansion of the array 1 also causes the proximal and distal intermediate members 9 and 13 to assume generally conical shapes and allow for the expansion of the array 1 against the stenosis being addressed. In the collapsed state the profile of the balloons 3 can approximate the diameter of the shaft 5 because extremely thin walled balloons can be employed, as will be described hereinafter.

Referring to FIGS. 2A and 2B, the balloons 3 constituting the array 1 are shown in an inflated state, as is the internal chamber 31 (in FIG. 2B). Each of the balloons 3 have side walls 3a, an inner wall 3b and an outer wall 3c. The balloons 3 are disposed in a cylindrical array around an axis. Each of the balloons 3 can share a common side wall 3a with the next adjacent balloon 3 to enable the expansion of the balloons 3 into the cylindrical array 1 upon inflation. The inner walls 3b form and surround an internal chamber 31. When the internal chamber 31 is open, the wall 30 is disposed against only about half of the inner wall 3b and allows body fluids to flow through openings 17. When inflation fluid is added through lumen 5a the wall 30 will move from one side of the internal chamber 31 to the other and cover the openings 17 (as shown in FIG. 2B). Body fluids thus cannot flow from one side of the catheter to the other but high forces can be exerted upon the stenosis being treated. The internal chamber 31, however, can be readily and periodically opened as necessitated to allow the flow of fluids while the array is kept inflated and urging against the body conduit which it is engaging. In closing the internal chamber 31 and moving from one side of the array to the other, the shaft 5 is moved from the side of the array to between the wall 30 and the inside of wall 3b and maintains its support of the catheter.

The wall thickness of each of the walls 3a, 3b and 3c and the wall 30 can be between about 0.0001 and 0.004 in. with 0.0003 to 0.002 in. being preferred. The deflated profile of the array 1 can be 0.003 in. or less. The interior of the array, that is the space between oppositely disposed inflated inner walls 3b, can be between about 0.02 and 2.0 in. With such a wide passageway body fluids can flow substantially unimpeded from one end of the array to the other and out without significant interruption. Thus a high flow rate of fluids can be achieved while still maintaining an adequate dilation force against the body conduit being treated.

Referring to FIG. 3, the proximal end of the catheter assembly, that is the proximal intermediate member 9, is shown. Each of the balloons 3 are arrayed cylindrically around the axis of the catheter. Each of the side walls 3a of the balloon 3 can be an integral part of an adjacent side wall 3a of an adjacent balloon 3. Each of the balloons 3 is connected to a supply of inflation fluid by means of a channel 11 formed within the proximal intermediate member 9. The channels 11 are separated from each other by webs 19 which form integral parts of the proximal intermediate member 9. A slit is made in one or more locations between channels 11 on each of the proximal and distal intermediate members 9 and 13 on a side opposite to the position of the sections 30a and 30b carried by wall 30 before the internal chamber 31 is inflated. The slits form opening(s) 17 through which body fluids can flow beneath the inner wall 3b of the array of balloons when the array 3 is inflated (see FIG. 1).

Each of the channels 11 in the proximal intermediate member 9 terminate in a central manifold area adjacent the proximal end of the catheter. A lumen 5c carries inflation fluid to the channels 11 to provide for inflation of the balloons 3. The distal intermediate member 13 can be a mirror image configuration of the proximal intermediate member 9, except that there is no need to carry inflation media within channels formed therein.

Inflation of the internal chamber 31 is accomplished by introducing an inflation fluid into lumen 5a. The lumen 5a terminated beneath the fold of wall 30 so that when the fluid is introduced the wall 30 will unfold and move from adjacent the inner walls 3b on one side of the array 1 to the other side. The lumen 5a can terminate where it meets wall 30. Lumen 5b can extend from one end of the catheter to the other to provide stability for the balloon and to house a removable trocar 12, if desired.

In FIG. 4, a cross-sectional view is shown of the interior of the proximal intermediate member 9. The channels 11 are shown as dotted lines within body of the webs 19 and as full lines within the cross-section. Each of the channels 11 are connected to the inflation lumen of the shaft 5 (not shown) so that inflation media can be delivered to the balloons. Several openings 17 are cut on each of the proximal and distal intermediate members 9 and 13 when the cylindrical array 1 of balloons 3 is inflated. Subsequent heating of the members causes the edges of the cuts to shrink to adjacent the outsides of the channels 11 to widen the openings 17. Wall 30 is disposed against the inner wall 3b and also against the inside of the proximal and distal intermediate members 30A and 30B. To allow for closing the catheter to the flow of body fluids, cuts are not made in webs that are covered by them.

To make the channels within the proximal and distal intermediate members, I have found that providing mild heating to these members while the channels 11 are filled with gas at about atmospheric pressure and while gas is also forced into the inflation lumen in shaft 5 causes dilation and stretching of the proximal and distal intermediate members 9 and 13. The operation enables cutting of slits in the web between two adjacent channels. The pressure exerted by the inflation of the balloons 3 against the side walls 3a and the mild heat causes the channels and the web to spread apart and shrink the edges to widen the openings. The Figure illustrates the proximal intermediate member 9 and a mirror image construction and the configuration can be embodied in the distal intermediate member 13. The openings in the distal intermediate member 13 can be substantially identical to openings 17 in the proximal intermediate member 9. Of course there is no need for the channels 11 to carry inflation media in the distal intermediate member.

In the manufacture of the herein described balloon assembly there is a requirement to create large openings near or on both ends of the balloon to enable the blood to flow from one end to the other without impeding its progress significantly. None of the channels can be blocked or cut through because in order to obtain adequate dilation force all of the channels must be inflated. Moreover, the openings should be made as close to the balloon as possible in order to reduce resistance to flow and it is essential that the openings be made as big as possible again to reduce flow resistance.

According to the present invention a tube is co-extruded with two or more dissimilar materials. Such materials have been described above. For example, one phase, a discreet phase, is formed of materials such as high density polyethylene. This phase can be drawn to form a tube with a plurality of channels in it. Co-extrusion of such materials is well known in the art and the shapes of the channels can be varied as desired by the operator. In FIG. 5, the drawn tubing used to form the balloons is shown. Openings 2 are radially arranged around the perimeter of the tubing and opening 4 is formed to cover about 50% of the tubing. It is disposed within the peripheral array of openings 4. All of the openings are arranged round a central opening 6.

The preferred method of manufacture of the balloons is then commenced by heating the tubing in the predetermined area where the balloons are to be formed and then simultaneously pressurizing both the channels and the areas of balloon formation and the interior of the balloon, that is the area adjacent inner walls 3b. The balloons will then expand to the desired diameter. After the balloons have been expanded, the proximate and distal intermediate members are formed by keeping each of these areas either simultaneously or sequentially inflated while not pressurizing the inside of the channels. In that way the balloons will expand but the spaces between the individual channels can be stretched and widened and one can safely cut the web between these channels to form the openings required for the flow of body fluids without severing the channels. A predetermined number of slits are made in the webs. The heating will cause the plastic to shrink and open the slits up to form big openings for the flow of fluids.

It is apparent that modifications and changes can be made within the spirit and scope of the present invention but it is my intention, however, only to be limited by the scope of the appended claims.

As my invention I claim:

1. A perfusion catheter for insertion into a body conduit and engagement thereof, said catheter comprising:

a shaft having at least two lumens for delivery of fluid inflation media;

a cylindrical array of radially disposed inflatable balloons disposed adjacent said shaft, said array having an inner and an outer surface, each balloon having a proximal end, said outer surface being adapted to engage said body conduit;

means to form a temporarily inflatable internal chamber within said cylindrical array, the force of inflation urging against said array of inflatable balloons;

means to inflate each of the balloons in said array, said means including a plurality of channels, each channel being in fluid flow relationship with one of said balloons and one of said lumens;

means to inflate temporarily said internal chamber, said internal chamber inflation means being in fluid flow relation with another of said lumens whereby to receive inflation fluid from said another lumen; and at least one opening between two adjacent channels to allow the flow of body fluids from one side of said cylindrical array, within said cylindrical array and thence out the other side when said internal chamber is not inflated.

2. The perfusion catheter according to claim 1 wherein the internal chamber is formed by a wall within said array, said wall being movable from adjacent one side of said array to the other side by the introduction of inflation fluid from said another lumen whereby to engage said inner surface to form said internal chamber and provide additional force for said catheter against said body conduit.

3. The perfusion catheter according to claim 1 wherein said channels extend to the proximal end of each of the balloons and the channels are separated from each other by webs whereby to form a proximal intermediate member.

4. The catheter according to claim 3 wherein the channels are separated from each other by a web, said web being disposed between adjacent channels, at least one of said webs having an opening therein to allow the flow of body fluids through said array and said chamber.

5. The catheter according to claim 4 wherein the channels and the webs together form a proximal intermediate member.

6. The catheter according to claim 5 further including a distal intermediate member attached to said array, said distal intermediate member having an opening therein to provide for the flow of body fluids.

7. The catheter according to claim 6 wherein said shaft extends through both said proximal and distal intermediate members.

8. The catheter according to claim 7 wherein said proximal intermediate member is joined to said shaft by a hub, said hub forming a manifold with a lumen in said shaft whereby fluid flow communication between said channels and said lumen is provided.

9. A catheter which allows the passage of blood through a body conduit while an array attached thereto is inflated, said catheter comprising:

a shaft having an internal lumen for the introduction of an inflation fluid;

a radially expandable, inflatable array of balloons attached to each other to form a cylinder disposed around said shaft, said array having an interior surface and a body conduit engaging surface the balloons of said array extending parallel to said shaft;

means to form a temporarily inflatable internal chamber within said cylindrical array, said internal chamber being adapted to engage and transmit force to said interior surface and thus to said body engaging surface;

means for connecting said array to said internal lumen of said shaft for enabling the introduction of inflation media to the balloons of said array and means for inflating said internal chamber; and, means for allowing the flow of body fluids between said shaft and said interior surface whereby the flow of body fluids through said conduit will not be prevented when said array is inflated and said internal chamber is not inflated.

10. The catheter according to claim 9 wherein the means for connecting the shaft to the cylindrical array of balloons are a plurality of channels spaced from each other by webs.

11. The catheter according to claim 10 wherein the means for allowing the flow of body fluids is at least one hole in a web between adjacent channels.

* * * * *